United States Patent [19]
Hasson

[11] Patent Number: 5,211,655
[45] Date of Patent: May 18, 1993

[54] MULTIPLE USE FORCEPS FOR ENDOSCOPY

[76] Inventor: Harrith M. Hasson, 2043 N. Sedgewick, Chicago, Ill. 60614

[21] Appl. No.: 880,560

[22] Filed: May 8, 1992

[51] Int. Cl.$^5$ ............................................. A61B 17/32
[52] U.S. Cl. .................................. 606/205; 606/170; 128/751
[58] Field of Search ........ 606/127, 128, 170, 205–211; 128/750, 751, 752, 755, 4–6

[56] References Cited

U.S. PATENT DOCUMENTS

| | | | |
|---|---|---|---|
| 4,084,594 | 4/1978 | Mosior | 606/174 |
| 4,122,856 | 10/1978 | Mosior et al. | 606/174 |
| 4,483,562 | 11/1984 | Schoolman | 606/174 |
| 4,662,371 | 5/1987 | Whipple et al. | 606/174 |
| 4,944,093 | 7/1990 | Falk | 606/174 |
| 5,009,661 | 4/1991 | Michelson | 606/205 |

FOREIGN PATENT DOCUMENTS

| | | | |
|---|---|---|---|
| 0418761 | 3/1991 | European Pat. Off. | 606/206 |
| 0450608 | 10/1991 | European Pat. Off. | 606/205 |
| 1091700 | 10/1960 | Fed. Rep. of Germany | 606/207 |
| 3802651 | 8/1989 | Fed. Rep. of Germany | 606/206 |
| 2022421 | 12/1979 | United Kingdom | 128/751 |

OTHER PUBLICATIONS

Catalog—Auto Suture Company Price List '92.

Primary Examiner—C. Fred Rosenbaum
Assistant Examiner—William W. Lewis
Attorney, Agent, or Firm—Wood, Phillips, VanSanten, Hoffman & Ertel

[57] ABSTRACT

A surgical instrument having a body with a rear proximal end and a forward distal end and a grip assembly attached to the body for facilitating holding and manipulation of the surgical instrument by the hand of a user. The grip assembly has front and rear handles that are movable relative to each other between first and second positions. The rear handle has a surface to be comfortably held in the palm of a hand holding the surgical instrument. A working tip operating mechanism is provided. A working tip is mounted to one of the operating mechanism and body at a first location on the body for movement between first and second positions. The rear handle is connected to the body so that the rear handle surface is in a fixed position relative to the first body location throughout the range of relative movement of the front and rear handles between their first and second positions. The front handle is connected to the operating mechanism so that the working tip moves between its first and second positions as an incident of the handles being moved between their first and second relative positions.

30 Claims, 7 Drawing Sheets

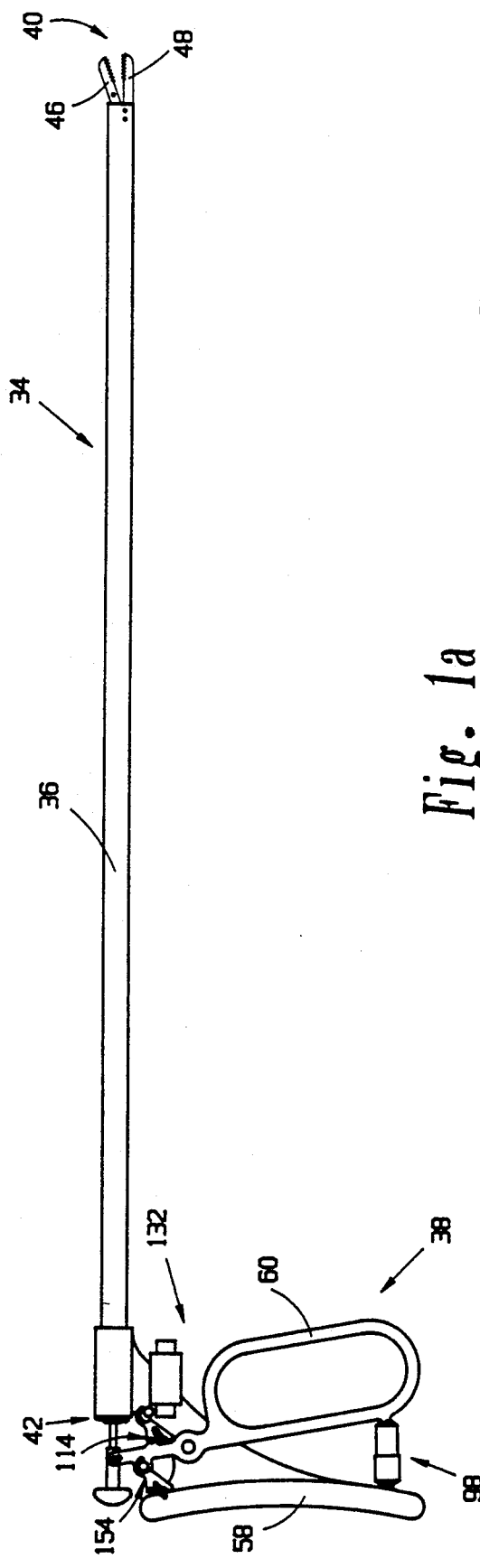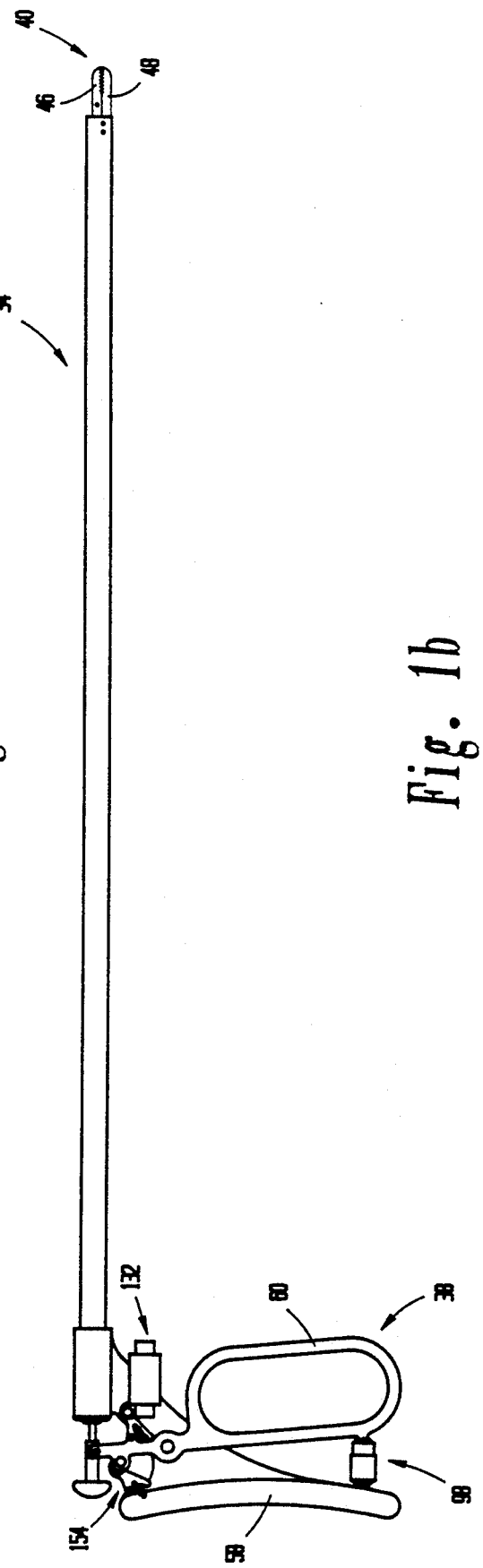
Fig. 1a
Fig. 1b

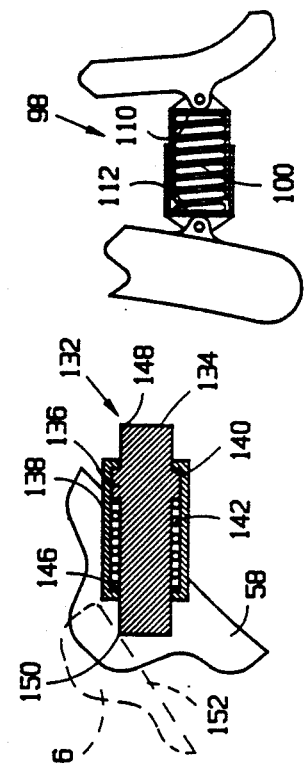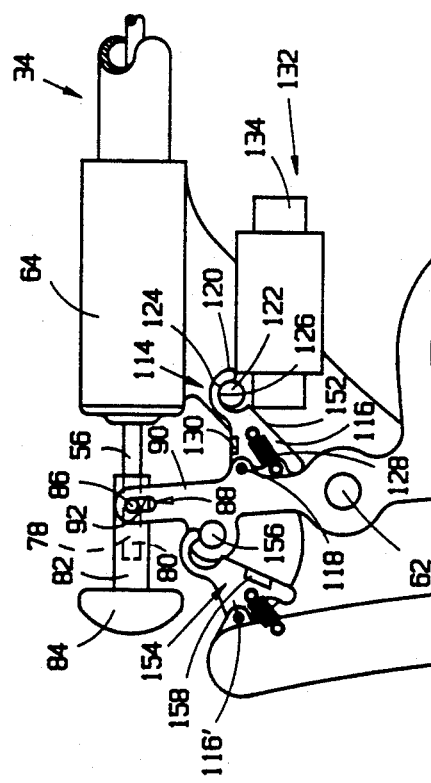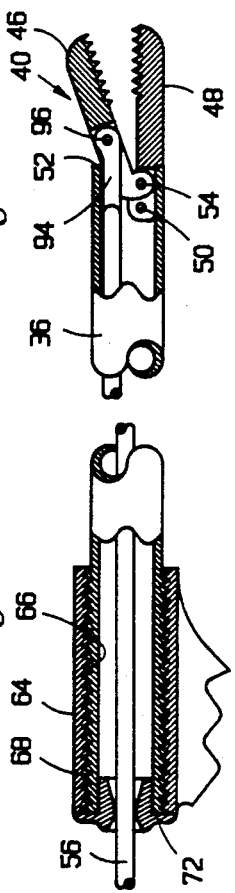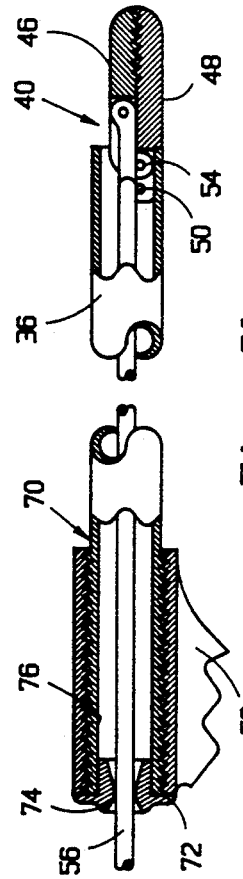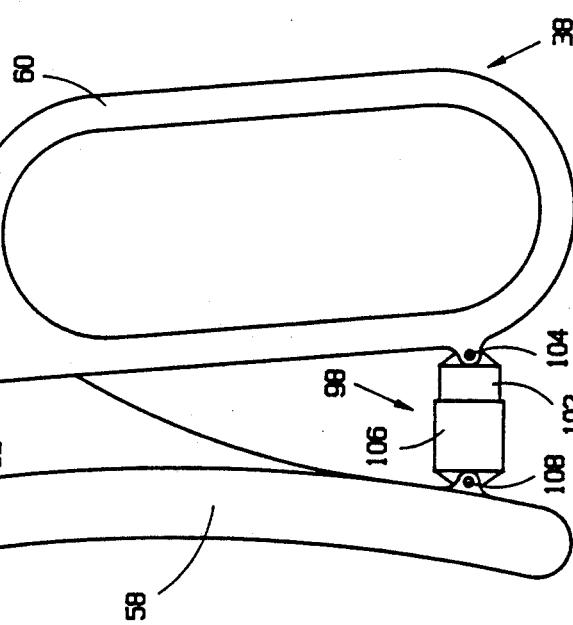

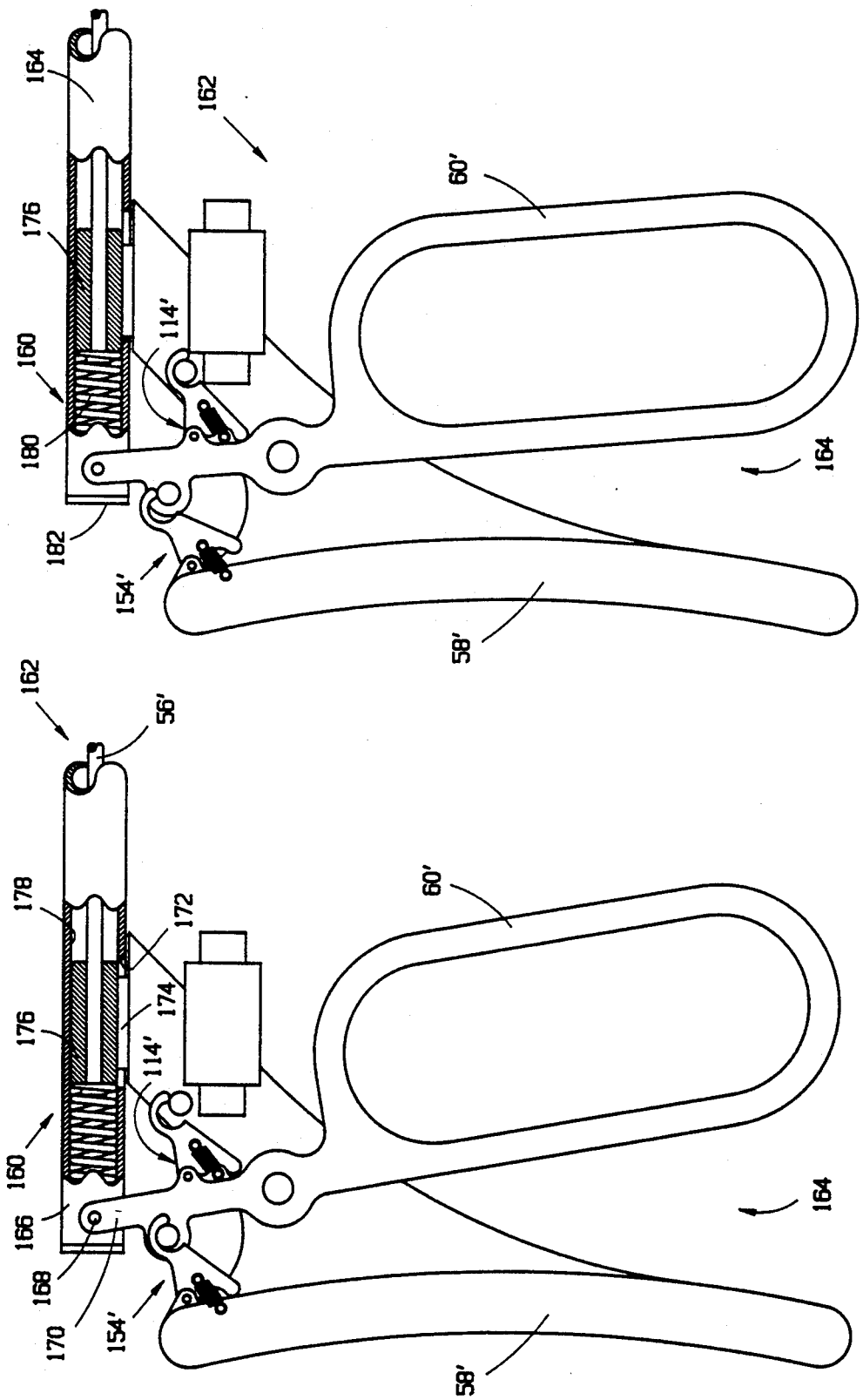

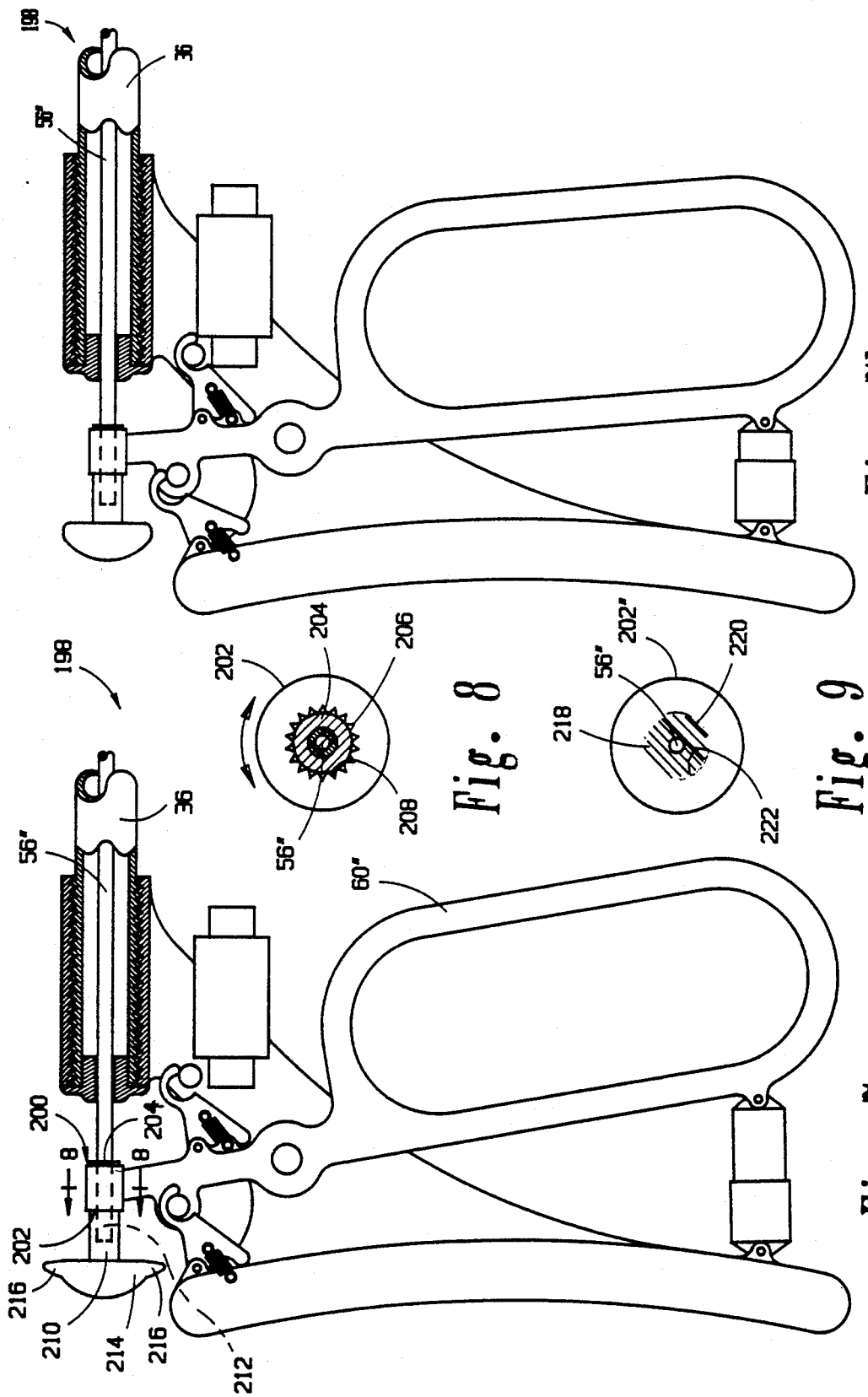

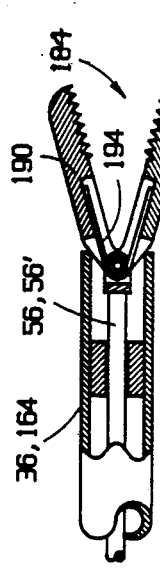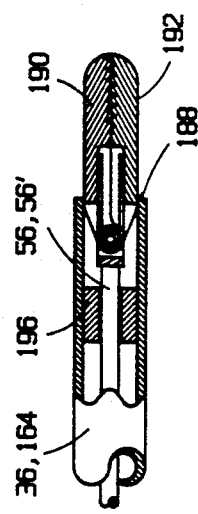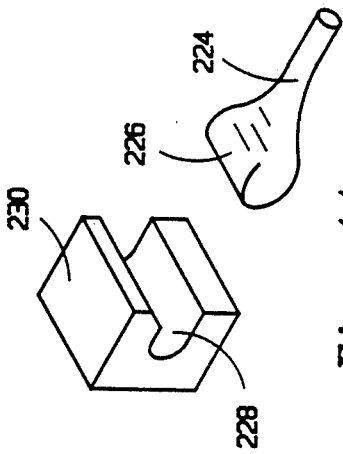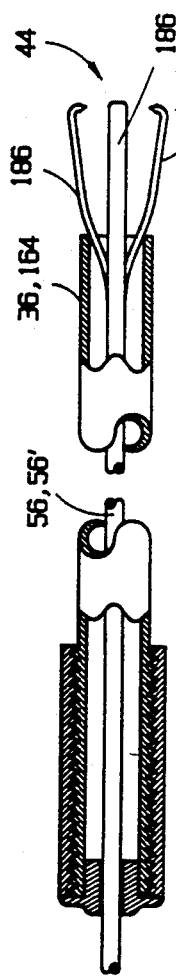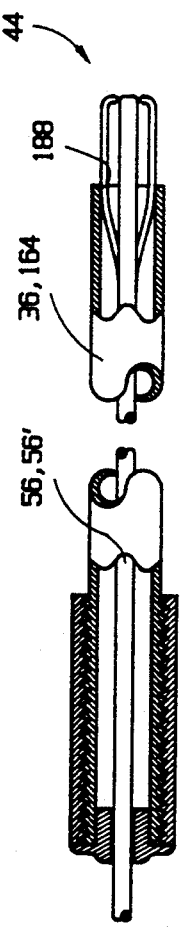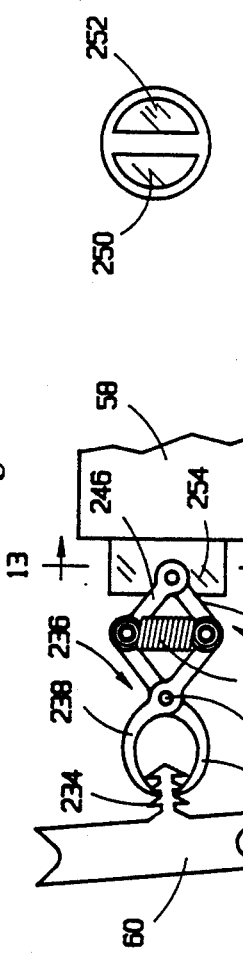

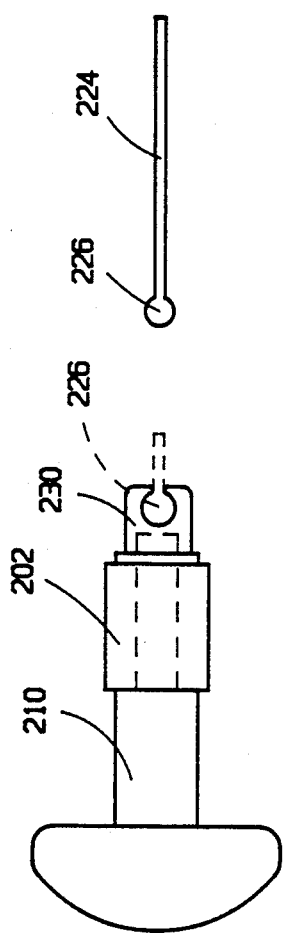
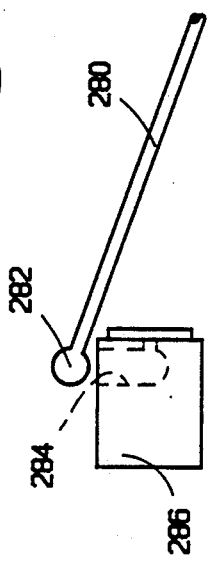
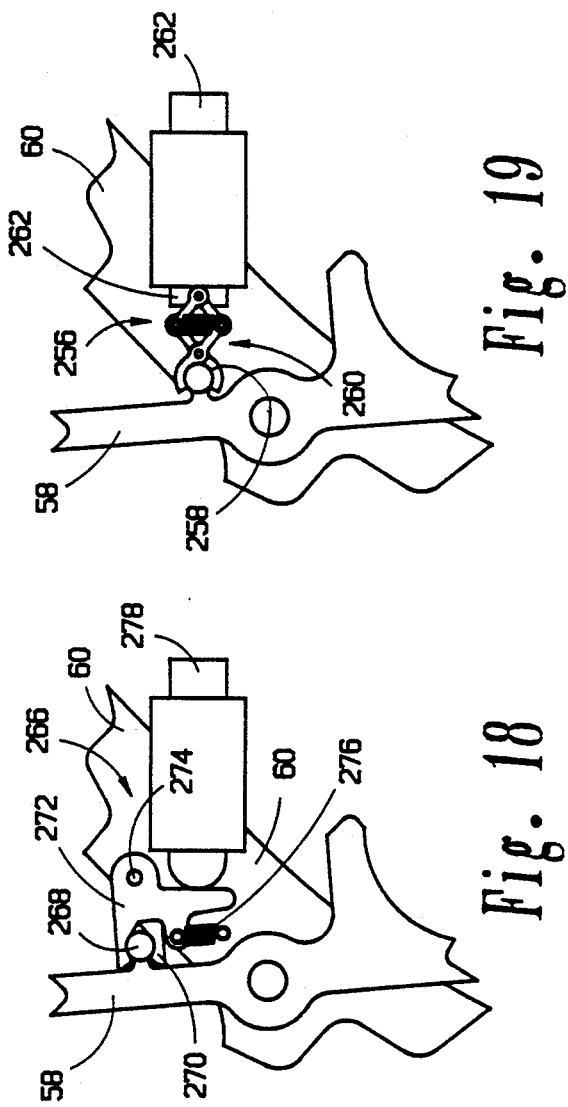

MULTIPLE USE FORCEPS FOR ENDOSCOPY

BACKGROUND OF THE INVENTION

1. Field of the Invention

This invention relates to surgical instruments and, more particularly, to an instrument that can be held and manipulated like a pistol and which is particularly adaptable for use as a forceps.

2. Background Art

Forceps-types of surgical instruments abound in the prior art. Certain of these instruments are suitable for the performance of laparoscopy, while others are not. It is common for those used in laparoscopy to have an elongate body, which is extendable through a trocar. At the distal end of the body are commonly one or two movable jaws which can be manipulated from the proximal end of the body. This jaw operation is commonly effected by holding a portion of the body between the index and middle fingers and pressing forwardly an operating rod or sleeve with the thumb in much the same manner as a plunger is depressed on a conventional syringe.

One difficulty with the above type of conventional instrument is that it is not firmly graspable within the hand of the user. It may be difficult or awkward for the user to firmly hold the instrument consistently in one position to carry out a procedure without hand fatigue. This is particularly true of those instruments that are operated by only the fingertips of the user. Further, nerve injury and/or paralysis may result to the thumb and/or fingers from repeated use of such an instrument.

Another problem with the above instrument is that the operating mechanism therefor is so configured that it is difficult for the user to exert a substantial force on the operating mechanism, particularly at some awkward angles in which the user may be required to place the instrument.

A further problem with the above type of instrument is that if the user wishes to lock the instrument in a particular position, as to maintain the jaws in a locked position, a set screw is commonly utilized. This requires the user to with one hand set the desired position for the jaw(s) and with the other hand tighten the set screw. To release the jaw(s), the user must stabilize the instrument with one hand and release the set screw with the other hand.

Another mechanism used to lock the jaws is a ratchet mechanism connected to the operating handles. Engaging the ratchet is usually not a problem. However, releasing the ratchet is often difficult and awkward and may require the use of both hands.

A still further problem with the above type of instruments is that they are generally one dimensional in function. That is, the working tip for each is generally adapted for but one function. For example, the working tip may be a pair of jaws or prongs. The user must keep on hand an inventory of different tools capable of carrying out each different procedure to be performed.

Still another problem with certain prior art surgical instruments of the type described above is that they do not lend themselves to cleaning and/or repair. Those units that are not readily disassembled may require an intricate cleaning process. In the event of a malfunction of the instrument, the entire instrument may have to be discarded.

SUMMARY OF THE INVENTION

The present invention is specifically directed to overcoming the above-enumerated problems in a novel and simple manner.

More specifically, the invention is directed to a surgical instrument having a body with a rear proximal end and a forward distal end and a grip assembly attached to the body for facilitating holding and manipulation of the surgical instrument by the hand of a user. The grip assembly has front and rear handles that are movable relative to each other between first and second positions. The rear handle has a surface to be comfortably held in the palm of a hand holding the surgical instrument. A working tip operating mechanism is provided. A working tip is mounted to one of the operating mechanism and body at a first location on the body for movement between first and second positions. The rear handle is connected to the body so that the rear handle surface is in a fixed position relative to the first body location throughout the range of relative movement of the front and rear handles between their first and second positions. The front handle is connected to the operating mechanism so that the working tip moves between its first and second positions as an incident of the handles being moved between their first and second relative positions.

In one form, the first location is at the distal end of the body.

With the above structure, it is possible to configure the handles to allow comfortable holding and manipulation of the instrument.

In one form, there is structure for releasably locking the handles in one of their first and second relative positions. The locking structure may also releasably lock the handles in a third relative position which is in the range of relative movement between the handles between their first and second relative positions.

The locking structure can take a variety of different forms. Preferably, first and second locking parts are provided, one each on the front and rear handles. In one form, the handles are automatically locked in one of their first and second positions as an incident of the handles being moved from the other of their first and second positions into the one of the first and second positions.

In one form, the locking parts each have a shoulder, which shoulders face and abut each other with the front and rear handles in a locked position. One of the locking parts has at least a portion that is deflectable to allow the handles to be placed in their locked position. In one form, the one locking part has a jaw that is pivotable between open and closed positions relative to the handle on which it is mounted and the jaw in its open position allows the handles to be placed in the one of their first and second relative positions so that the jaw can be moved to its closed position to hold the handles in their locked position.

For the comfort and convenience of the user, the front handle preferably has a loop to allow passage therethrough of at least one manipulating finger, and preferably a plurality of fingers of the user.

To facilitate repair and/or cleaning of the device, the body may be removably assembled to the rear handle. This removable connection may be accomplished by making a threaded connection between these parts.

In one form, the operating mechanism has a rod that is extendable in a fore and aft direction relative to the body. The rod is, in one form, removably connected to the front handle so that it as well might be disassembled.

In addition to allowing disassembly, as for cleaning and repair, the disassembly allows the substitution of bodies with different working tips. For example, the working tip could be a pair of cooperating jaws, prongs, or other type of instrument employing a movable member.

With the inventive device, one can conveniently hold the instrument like a pistol. The front handle can be conveniently moved, and preferably pivoted, relative to the rear handle by squeezing the front handle towards the rear handle. This effects operation of the working tip without changing the location of the working tip relative to the rear handle. The invention also contemplates a mechanism to release the locking structure with the hand normally gripping the instrument for operation.

In one form, a depressible button is provided on the instrument, and preferably on the rear handle, and is operable by a finger, such as the index finger, with the hand of the user grasping the handles. The user is thus afforded the convenience of locking, manipulating and releasing the locking structure with a single hand.

The invention further contemplates a surgical instrument having an elongate body with a rear proximal end and a forward distal end, a grip assembly for holding the surgical instrument, a first working tip positionable selectively in first and second positions, a working tip operating mechanism including an elongate operating rod, structure for connecting the operating rod to at least one of the body and grip assembly for movement to the between first and second positions, cooperating structure on the operating rod and working tip for positioning the working tip in its first position as an incident of the operating rod moving from one of its first and second positions into the other of its first and second positions and for positioning the working tip in its second position as an incident of the operating rod moving from the other of its first and second positions into the one of its first and second positions.

In one form, there is structure for allowing the operating rod to be rotated about its length to place the working tip selectively in a plurality of different positions relative to at least one of the body and grip assemblies.

In another form, structure is provided for releasably connecting the first working tip to the grip assembly to allow replacement of the first working tip.

The invention also contemplates the combination of a second working tip that is releasably connectable to the grip assembly. Preferably, the second working tip has a different configuration than the first working tip.

In another form of the invention, the grip assembly includes a handle connected to the body so as to define a generally L shape with the body.

BRIEF DESCRIPTION OF THE DRAWINGS

FIG. 1a is a side elevation view of a surgical instrument, according to the present invention, and having a working tip, consisting of cooperating jaws, shown in an open position;

FIG. 1b is a view as in FIG. 1a with the jaws in a closed position;

FIG. 2 is an enlarged, fragmentary, elevation view of a grip assembly for holding and operating the instrument of FIGS. 1a and 1b from a location remote from the jaws;

FIG. 3 is a fragmentary, cross-sectional view of a button for releasing a locking mechanism that holds cooperating handles on the grip assembly in fixed relative relationship;

FIG. 4 is a fragmentary cross-sectional view of a biasing assembly for urging the handles normally away from each other to place the jaws in an open position;

FIG. 5a is a fragmentary cross-sectional view of part of an operating mechanism for the jaws, which are shown in an open position;

FIG. 5b is a view as in FIG. 5a with the jaws in a closed position;

FIG. 6a is a fragmentary, partial cross-sectional view of a modified form of operating mechanism for the jaws, according to the present invention, and showing the handles on a grip assembly situated to place the jaws in an open position;

FIG. 6b is a view as in FIG. 6a with the jaws in a closed position;

FIG. 7a is a fragmentary, partial cross-sectional view of a further modified form of grip assembly and jaw operating mechanism with the handles on the grip assembly positioned to place the jaws in an open position;

FIG. 7b is a view as in FIG. 7a with the handles situated to position the jaws in a closed position;

FIG. 8 is a cross-sectional view of a connection between part of an operating mechanism and the grip assembly to allow an operating rod on the operating mechanism to be reoriented by pivoting thereof about the length of the instrument;

FIG. 9 is a view as in FIG. 8 showing a modified form of structure for allowing rotation of the operating rod relative to the grip assembly;

FIG. 10a is a fragmentary, partial cross-sectional view of an operating mechanism, according to the present invention, and showing a plurality of prongs substituted for the jaws, previously described, with the prongs shown in an open position;

FIG. 10b is a view as in FIG. 10a with the prongs shown in a closed position;

FIG. 11a is a fragmentary, partial cross-sectional view of a modified form of jaw, according to the present invention, with the jaws shown in an open position;

FIG. 11b is a view as in FIG. 11a, with the jaws in a closed position;

FIG. 12 is a fragmentary, side elevation view of an alternative form of locking mechanism for releasably holding the handles on the grip assembly in a fixed relative relationship;

FIG. 13 is a cross-sectional view of the locking mechanism taken along line 13—13 of FIG. 12;

FIG. 14 is an exploded perspective view of a mounting block for releasably connecting to an end of an operating rod associated with the operating mechanism, which allows the operating rod to be rotated to reposition a working tip thereon;

FIG. 15 is a side elevation view of the mounting block and operating rod, with the operating rod shown operatively connected to the mounting block in phantom lines and disassembled in solid lines;

FIG. 16 is a side elevation view of a modified form of connection for the mounting rod in the form of a ball and socket arrangement and showing the operating rod in a disassembled state;

FIG. 17 is a view as in FIG. 16 with the operating rod in operative position;

FIG. 18 is a fragmentary side elevation view of a modified form of locking mechanism to releasably maintain the handles in a fixed relative relationship;

FIG. 19 is a fragmentary elevation view of a still further modified form of locking mechanism for maintaining the handles on the grip assembly in a fixed relative relationship;

DETAILED DESCRIPTION OF THE DRAWINGS

Figure 20A:
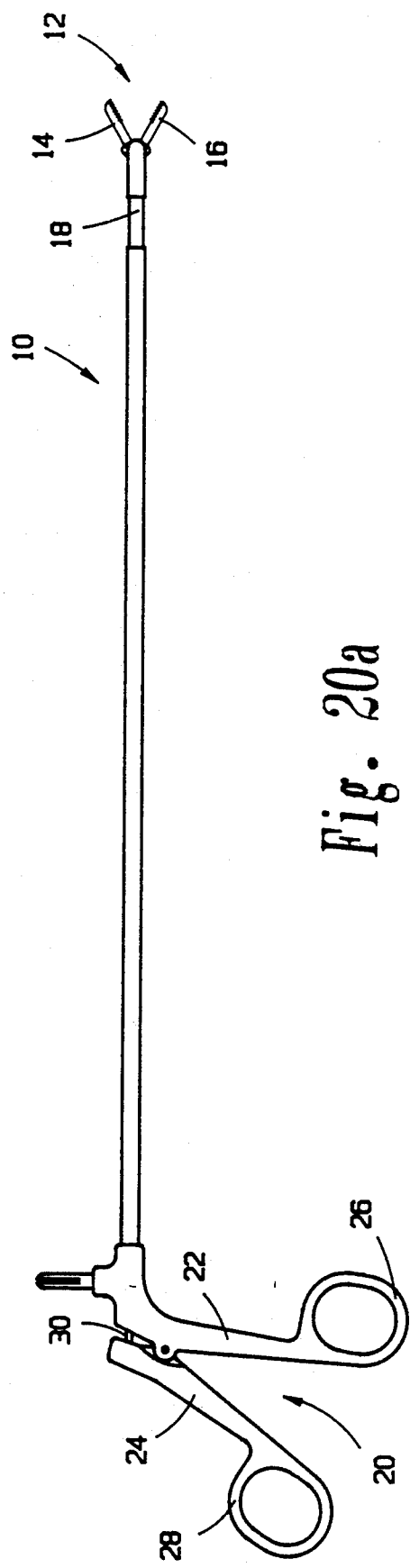
FIG. 20a is a side elevation view of a prior art instrument with jaws thereon shown in an open state.
Figure 20B:
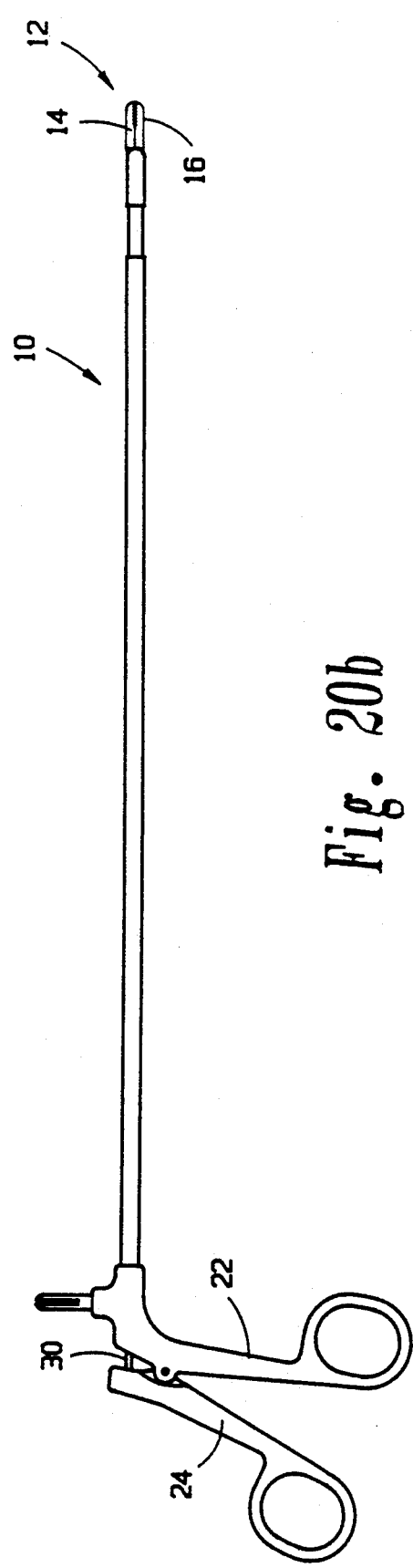
FIG. 20b is a view as in FIG. 20a with the jaws shown in a closed state.

One type of prior art instrument, over which the present invention improves, is shown at 10 in FIGS. 20a and 20b. The instrument 10 consists of a working tip at 12, consisting of relatively movable and cooperating jaws 14, 16, at the distal end 18 of the instrument 10, and a grip assembly at 20, consisting of cooperating front and rear handles 22, 24, respectively, at the proximal instrument end. The handles 22, 24 are relatively movable to reposition the jaws 14, 16 between the open position, shown in FIG. 20a and the closed position, shown in FIG. 20b. The handles 22, 24 each have a finger loop 26, 28 to accept the tips of, for example, the thumb and middle finger of the user. By squeezing the handles 22, 24 towards each other, an operating rod 30 is repositioned to urge the jaws 14, 16 into the closed position of FIG. 20b. The closing force on the jaws 14, 16 is determined by the amount of pressure applied through the handles 22, 24. Opening of the jaws 14, 16 is accomplished by spreading the handles 22, 24 away from each other.

The instrument 10 has numerous drawbacks. First of all, it does not lend itself to disassembly. Failure of any part of the instrument may result in the entire instrument's being rendered unusable. In spite of the expense of such surgical instruments, repair may not be feasible. This inability to readily disassemble the instrument 10 also makes it difficult to clean.

A further drawback with the instrument 10 is that it is generally quite uncomfortable to operate. Operation of the instrument 10 is effected through just the fingertips, with the fingertips providing the only support in the user's hand. Consequently, the instrument 10 is inherently unstable during use. Additionally, the user's hand tends to fatigue by reason of having to maintain a constant pressure on the handles 22, 24, during operation, to keep the jaws 14, 16 closed, to thereby effectively hold an object therebetween. Fatigue is particularly a problem given that just two fingers are used to squeeze the handles 22, 24. Nerve injury and paralysis to the thumb and/or fingers can occur.

A further drawback with the instrument 10 is that there is no provision to lock the jaws 14, 16 in a closed position. Instead, the pressure varies in accordance with the pressure applied on the handles 22, 24. As the user repositions the instrument, this pressure must be maintained to avoid losing a grip on an object held by the jaws 14, 16. Inevitably, repositioning of the user's hand and/or arm results in a variation of the pressure applied through the handles 22, 24. This may result in shifting of an object between the jaws 14, 16, or escape altogether of the object from the jaws 14, 16.

A first form of instrument, according to the present invention, is shown at 34 in FIGS. 1a-5b. The instrument 34 consists of a cylindrical body 36, a grip assembly at 38, a working tip at 40, and an operating mechanism at 42 for effecting repositioning of the working tip 40 as an incident of the grip assembly 38 being operated.

The working tip 40 disclosed is exemplary of the many types of working tips that can be employed with the present invention. One alternative working tip is shown at 44 in FIGS. 10a and 10b, which working tip 44 will be discussed in detail below.

The jawed working tip 40 consists of first and second, cooperating, toothed jaws 46, 48, which are movable selectively between an open position, shown in FIGS. 1a and 5a, and a closed position, shown in FIGS. 1b and 5b. More particularly, the jaw 48 is fixedly connected to the body 36 by a pin 50, so as to project in cantilever fashion from the forward, distal free edge 52 of the body 36. The other jaw 46 is connected for pivoting relative to the jaw 48 by a pin 54.

The jaw 46 is moved relative to the jaw 48 by an elongate operating rod 56, which extends through the body 36. The position of the operating rod 56 is controlled by the grip assembly 38. Advancement of the rod 56, in a left-to-right direction in FIGS. 1a-5b, causes the jaw 46 to pivot in a clockwise direction around the pin 54 to the closed position of FIG. 1b and 5b. Opposite movement of the operating rod 56 pivots the jaw 46 in a counterclockwise direction about the pin 54 to the open position of FIGS. 1a and 5a.

The grip assembly 38, through which the operating rod 56 is controlled, consists of a rear handle 58, which is contoured to comfortably fit in the palm of a user's hand, and a front handle 60, in the form of a loop, which handle 60 is connected at its midportion for pivoting movement relative to the grip 58 by a pin 62. The loop 60 can be made sufficiently large to comfortably accept the user's four fingers which can be used to positively squeeze the front handle 60 towards the rear handle 58 to effect closing of the jaws 46, 48.

The rear handle 58 extends upwardly to a cylindrical mounting element 64, which is fixedly attached thereto. The mounting element 64 has threads 66, internally thereof, to mate with threads 68 at the proximal end 70 of the body 36. This facilitates assembly as well as separation of the body 36, to facilitate cleaning and/or repair of the instrument 34 as well as the changing of the body 36 to allow replacement thereof by a body having a different size or configuration of working tip.

The operating rod 56 projects rearwardly from the proximal edge 72 of the body 36. A resilient gasket 74 seals the annular space between the operating rod 56 and radially inwardly facing surface 76 defined by the body 36 and also provides a support for the body 36.

The rear end 78 of the operating rod 56 is threaded to be removably engaged within a threaded blind bore 80 in a mounting element 82. The mounting element 82 has an enlarged head 84 to facilitate rotation thereof relative to the operating rod 56, to effect engagement therebetween. With this arrangement, the mounting element 82 can be disassembled from the operating rod 56, whereupon the body 36, with the working tip 40 thereon, can be disassembled from the grip assembly 38.

The mounting element 82 has a laterally projecting pin 86 for reception in an oval slot 88 in the upper end of the front handle 60. Upon squeezing the front handle 60 towards the rear handle 58, the upper end 90 of the front handle 60 is caused to rotate in a clockwise direction about the pin 62. As this occurs, the surface 92 bounding the slot 88 drives the pin 86, and thereby the rod 56, towards the right in FIGS. 2, 5a and 5b. The distal end 94 of the rod 56, which is pivotably connected to the jaw 46 through a pin 96, drives the jaw 46 into the closed position of FIGS. 1b and 5b. Movement of the handles 58, 60 away from each other effects opening of the jaws 46, 48.

The jaws 46, 48 are normally biased to an open position by a spring assembly at 98 acting upon the handles 58, 60. The spring assembly consists of a compression coil spring 100 that normally biases the handles 58, 60 away from each other. The spring 100 is confined in an envelope defined by a cup-shaped element 102, pivotably connected by a pin 104, to the front handle 60 and opening in one direction and an oppositely opening, cup-shaped element 106, pivotably connected to the rear handle 58 by a pin 108. The cup-shaped elements 102, 106 are telescopingly received, one within the other, so that the spring 100 acts between oppositely facing surfaces 110, 112 on the elements 102, 106, respectively to thereby drive the handles 58, 60 away from each other.

A releasable locking mechanism is provided at 114 for holding the handles 58, 60 in fixed relationship with the jaws 46, 48 in a closed position. This avoids the user's having to maintain a constant pressure on the handles 58, 60. The locking mechanism 114 consists of a latch element 116 that is pivoted on, and relative to, the front handle 60 by a laterally extending pin 118. The latch element 116 has a hooked end 120 to receive a locking post 122 on the rear grip 58. Oppositely facing shoulders 124, 126 on the post 122 and latch element 116, respectively, maintain the handles 58, 60 in the position shown in FIG. 2. A tension coil spring 128 normally urges the latch element 116 in a clockwise direction about the mounting pin 118. As the handles 58, 60 are moved from the FIG. 1a position towards the FIG. 1b position therefor, the hooked end 120 is cammed over the locking post 122 until the FIG. 1b position is realized, at which time the latch element 116 pivots in a clockwise direction over the locking post 122 to seat the locking post 122 as shown in FIG. 2.

In one form, an integral, laterally extending tab 130 on the latch element 116 facilitates manual release thereof to allow the handles 58, 60 to move away from each other to situate the jaws 46, 48 in their open position.

In a preferred form, the latch element 116 is released from its engaged position of FIG. 2 by a mechanism at 132. The mechanism 132 consists of a release button 134 that can be depressed as by the index finger on the hand holding the grip assembly 38. The button 134 has an enlarged midportion 136 which is guided in a fore and aft direction within a sleeve 138 affixed to the rear handle 58. A rearwardly facing shoulder 140 on the sleeve 138 limits forward movement of the button 134. A spring 142 surrounds the button 134 and acts between the enlargement 136 on the button 134 and a forwardly facing shoulder 146 defined by an inturned portion of the sleeve 138 to normally drive the button 134 forwardly into the position shown in FIG. 3. By pressing on the forward portion 148 of the button 134, a rear corner 150, projecting out of the sleeve 138, encounters a cam surface 152 on the latch element 116 to thereby effect release thereof by movement of the latch element 116 in a counterclockwise direction about the pin 118.

A similarly operating locking mechanism is provided at 154 to releasably lock the handles 58, 60 so that the jaws are in their open position. A similar latch element 116' on the upper portion of the rear handle 58 is engageable with a locking post 156 on the upper portion of the forward handle 60. A tab 158 is provided to effect release of the latching element 116'.

With the inventive instrument 34, the user can comfortably hold the grip assembly 38 and effect repositioning and operation of the instrument 34. In the embodiment shown in FIGS. 1a through 5b, the plane of movement of the jaws 46, 48 is aligned with the plane of movement of the handles 58, 60 so that the user is constantly aware of the orientation of the jaws 46, 48 even when the same are not in view. The L-shaped arrangement of the grip assembly 38 and body 36 permits operation of the device in much the same manner as a pistol. The user is thus able to comfortably hold the instrument and exert and maintain a substantial force on the jaws 46, 48 without experiencing hand or arm fatigue.

A modified form of operating mechanism for the instrument is shown at 160 on an instrument 162 in FIGS. 6a and 6b. Corresponding elements on the different embodiments described below are identified by the same number with the use of a "'" or "''". The instrument 162 has a grip assembly 164 consisting of grips 58', 60', corresponding to the grips 58, 60 on the instrument 134. Locking mechanisms 114' 154' are provided to respectively maintain the grips 58', 60' releasably in positions corresponding to closed and open positions for the working tip (not shown). The spring assembly 98 in the instrument 34 is omitted from the instrument 162.

The primary distinction between the instrument 162 and the instrument 34, previously described, is in the operating mechanism 160. More particularly, a body 164 extends rearwardly to a greater extent than the corresponding body 36 on the instrument 34. The rear body end 166 is pivotably connected by a pin 168 to the upper portion 170 of the grip 60'. The body 164 has an elongate slot 172 extending therethrough for reception of a guide neck 174 projecting upwardly from the handle 58' and connecting fixedly to a slider 176. The slider 176 is guided in a fore and aft direction against the inside surface 178 of the body 164. The slot 172 is sufficiently long in a fore and aft direction to allow the necessary range of shifting of the neck 174 therewithin to place a working tip in both fully open and fully closed positions.

An operating rod 56, 56' is fixedly embedded in the slider 176. The slider 176 is normally biased forwardly by a coil spring 180 acting between a rear wall 182 on the body 36, 164 and the slider 176.

With this arrangement, squeezing of the handles 58', 60' causes the body 36, 164 to be advanced forwardly relative to the slider 176 and operating rod 156', carried thereby. This particular operating mechanism is useful to operate, among others, working tips of the type such as the working tip 44, shown in FIGS. 10a and 10b, and the working tip 184, shown in FIGS. 11a and 11b.

More particularly, the working tip 44 consists of four prongs 186, which are integrally connected to the operating rod 56, 56'. The prongs 186 are normally biased away from each other to an open position, shown in FIG. 10a. By drawing the operating rod 56, 56' from right to left in FIGS. 10a and 10b into the body 36, 164, or by alternatively advancing the body 36, 164 over the prongs 186 from left to right in FIGS. 10a and 10b, the prongs 186 are caused to be compressed to a closed position by the annular corner 188 on the body 36, 164. The invention contemplates for this embodiment, as in most embodiments herein, that the rod 56, 56' could be held stationary and the body 36, 164 advanced thereover.

In FIGS. 11a and 11b, the working tip 184 consists of cooperating jaws 190, 192, which are normally spring biased by a torsion spring 194 to an open position. The jaw pair 190, 192 is connected to the distal end of the operating rod 56, 56' and is closed upon the operating rod 56, 56' being drawn from right to left so that the corner 188 of the body 36, 164 engages and progressively cams the jaws 190, 192 towards a closed position therefor, as shown in FIG. 11b. A stabilizing element 196 is provided within the body 36, 164 to prevent radial shifting of the distal end of the operating rod 56, 56'.

The invention contemplates using the working tips 44, 184 in place of the working tip 40 in the instrument 34. This results in the working tip 44, 184 being normally closed in the FIG. 12 position for the instrument 34, and open in the FIG. 1b position.

A slightly modified form of instrument, according to the present invention, is shown at 198 in FIGS. 7a-9. The instrument 198 is substantially identical to the instrument 34, with the principal distinction residing in the connection 200 in the operating rod 56'' and the front handle 60''.

More particularly, a mounting element 202 is fixedly attached to the upper end of the handle 60''. The operating rod 56'' is fixedly embedded in a rubber base 204 having equidistantly spaced, triangular projections 206 integrally formed therewith. The mounting element 202 has recesses 208 corresponding to the projections 206 on the base 204. The projections 206 are firmly held in the recesses 208 to inhibit relative rotation between the mounting element 202 and base 204. The rubber, or other material making up the base 204, is sufficiently flexible that the base 204 can be rotated within the mounting element 202 upon a predetermined torque being applied thereto.

A mounting element 210 threadably engages the rear end 212 of the operating rod 56''. The mounting element 210 has an enlarged head 214 with projections 216 thereon to facilitate rotation of the mounting element 210. By rotating the mounting element 210, the base 204 is caused to turn in the mounting element 202, which effects rotation of the operating rod 56'' to thereby change the orientation of the working tip (not shown) connected to the operating rod 56''. Thus the user can select the desired orientation of the working tip. This orientation will be releasably maintained by the cooperating projections 206 and recesses 208.

In FIG. 9, the operating rod 56'' is shown embedded in a base 218 that has an uninterrupted, cylindrical, outer surface 220 closely frictionally received within a cylindrical surface 222 defined by an operating element 202''. Friction between the base 218 and mounting element 202'' is sufficient to releasably hold the position of the operating rod 56'' relative to the body 36. The base 218 is more prone to slipping than the base 204 in FIG. 8 but may be suitable in certain environments.

An alternative connection for an operating rod 224 is shown in FIGS. 14 and 15 to allow the operating rod 224 to be rotatably mounted. The operating rod 224 has an integrally formed, enlarged, cylindrical base 226 which can be laterally directed into a correspondingly configured through opening 228 in a mounting block 230. The mounting block 230 can be threadably engaged with the mounting element 210, to be borne against the mounting element 202, which is thus frictionally held captive between the mounting element 210 and the mounting block 230. By unscrewing the mounting element 210, the mounting block 230 can be readily rotated to a desired position, which can then be fixed by retightening the mounting element 210.

FIGS. 12, 13, 18 and 19 show modified forms of locking mechanism that can be used in place of the locking mechanisms 114, 154, previously described. The locking mechanism 232, shown in FIGS. 12 and 13, consists of a stepped projection 234 on the forward handle 60 and a cooperating clamping linkage 236 on the rear handle 58. The linkage 236 consists of cooperating jaws 238, 240 pivoted at their midportions by a pin 242 and normally urged into a closed position by a tension spring 244 connected between the jaws 238, 240. Drive links 246, 248 are pivotably connected between the legs 250, 252 of a bifurcated post 254 on the handle 58. As the handles 58, 60 are squeezed against each other, the jaws 248, 240 are progressively cammed over the projection 234 to releasably maintain the handles 58, 60 in a plurality of different positions.

FIG. 19 shows an operating mechanism 256 that is substantially the same as the mechanism 232, with the principal distinctions being that a cylindrical locking post 258 is substituted for the projection 234 and the linkage 260, corresponding to the linkage 236, is connected to a release button 262, which is depressible to open the mechanism 256 to allow separation of the handles 58, 60.

In FIG. 18, a modified form of locking mechanism is shown at 266. The locking mechanism consists of a cylindrical post 268 on the handle 58 to be releasably engaged by a jaw pair 270, 272. The jaw 270 is fixed to the handle 60, with the jaw 272 being pivotable relative to the handle 60 about a pin 274. A tension spring 276 normally urges the jaw 272 in a counterclockwise direction about the pin 274 into a closed position. As the handles 58, 60 are squeezed towards each other, the post 268 wedges the jaw 272 in a clockwise direction about the pin 274 to effect opening of the jaw pair 270, 272. Once the post 268 seats in the jaws 270, 272, the spring 276 urges the jaw 272 in a counterclockwise direction to capture the post 268 between the jaws 270, 272. Release of the jaws 270, 272 is effected through a spring-biased, depressible button 278.

A modified form of connection of an operating rod 280 is shown in FIGS. 16 and 17. The operating rod 280 has an integral ball connector 282 which can be dropped into an upwardly opening slot 284 on a connector 286, corresponding to the mounting element 202. Thus the user can simply squeeze the handle 58, 60 towards each other and drop the rod ball 282 into the socket 284 to create a ball and socket connection. Disassembly is as readily accomplished for purposes of repair and/or cleaning.

It can be seen that the inventive instrument can be comfortably held and operated. The pistol-type grip assembly facilitates squeezing of the handles. While firmly grasping the handles, the user can conveniently access buttons/tabs to release handle locking mechanisms. The instrument is readily assembled and disassembled for repair and/or cleaning. At the same time, one subassembly can be used to accommodate a wide variety of working tips.

The foregoing disclosure of specific embodiments is intended to be illustrative of the broad concepts comprehended by the invention.

I claim:

1. A surgical instrument comprising:
   a body having a rear proximal end and a forward distal end;
   a grip assembly attached to the body for facilitating holding and manipulation of the surgical instrument by the hand of a user,
   said grip assembly including a rear handle and a front handle with said front and rear handles being movable relative to each other between first and second position,
   said rear handle having a surface to be held in the palm of a hand holding the surgical instrument;
   a working tip operating mechanism;
   a working tip mounted to at least one of said operating mechanism and body at a first location on said body for movement between first and second position;
   means for connecting the rear handle to the body so that the rear handle surface is in a fixed position relative to the first body location throughout the range of relative movement of the front and rear handles between their first and second positions;
   means for connecting the front handle to the operating mechanism and for causing the working tip to move between its first and second positions as an incident of the handles being moved between their first and second relative positions;
   means for releasably locking the front and rear handles in a fixed relationship; and
   means for releasing the handle locking means,
   said releasing means comprising a button that is movable between normal and release position,
   said button being situated forwardly of said rear handle surface to be engagable by one of a user's finger that is engagable with the front handle with the grip assembly being normally held by the hand of a user.

2. The surgical instrument according to claim 1 wherein the first location is at the distal end of the body.

3. The surgical instrument according to claim 1 where said handle locking means comprises means for releasably locking the handles in one of their first and second relative positions.

4. The surgical instrument according to claim 3 wherein said locking means includes means for releasably locking the handles in a third relative position which is in the range of relative movement between the handles between their first and second relative positions.

5. The surgical instrument according to claim 3 wherein the locking means comprises first and second engagable locking parts, one each on the front and rear handles.

6. The surgical instrument according to claim 3 wherein said locking means includes means for automatically locking the handles in the one of the first and second positions as an incident of the handles being moved from the other of the their first and second positions into the one of their first and second positions.

7. The surgical instrument according to claim 1 wherein said front handle has a loop to allow passage therethrough of a plurality of fingers of a user.

8. The surgical instrument according to claim 1 wherein there are cooperating means on the rear handle and body for releasably maintaining the body in a fixed, assembled position on the rear handle.

9. The surgical instrument according to claim 8 wherein the cooperating means on the rear handle and body comprises means for threadably connecting the body and rear handle.

10. The surgical instrument according to claim 1 wherein said operating mechanism includes an operating rod that is extendable in a fore and aft direction relative to the body as an incident of the handles being moved between their first and second positions.

11. The surgical instrument according to claim 10 wherein the operating rod is removably connected to the front handle.

12. The surgical instrument according to claim 10 wherein said body comprises a sleeve and at least a part of the operating mechanism extends through the sleeve.

13. The surgical instrument according to claim 1 wherein the working tip includes a jaw that is pivotably connected to the body.

14. The surgical instrument according to claim 1 where the button is mounted for movement from front to rear relative to said body in moving from its normal position into its release position.

15. The surgical instrument according to claim 1 including first means for locking the front and rear handles in one relative position and a second locking means separate from said first locking means for locking the front and rear handles in another relative position.

16. The surgical instrument according to claim 1 including means for releasably locking the working tip in one of its first and second positions.

17. A surgical instrument comprising:
    a body having a rear proximal end and a forward distal end;
    a grip assembly attached to the body for facilitating holding and manipulation of the surgical instrument by the hand of a user,
    said grip assembly including a rear handle and a front handle with said front and rear handles being movable relative to each other between first and second positions,
    said rear handle having a surface to be held in the palm of a hand holding the surgical instrument;
    a working tip mounted to at least one of said operating mechanism and body at a first location on said body for movement between first and second positions;
    means for connecting the rear handle to the body so that the rear handle surface is in a fixed position relative to the first body location throughout the range of relative movement of the front and rear handles between their first and second positions;
    means for connecting the front handle to the operating mechanism and for causing the working tip to move between its first and second positions as an incident of the handles being moved between their first and second relative positions; and
    means for releasably locking the handles in one of their first and second relative positions,
    wherein the locking means comprises first and second engagable locking parts, one each on the front and rear handles,
    wherein one of the first and second locking parts has a first shoulder and the other of the first and second locking parts has a second shoulder which shoulders face and abut each other with the front and rear handles in a locked position to releasably maintain the handles in the one of their first and second relative positions.

18. The surgical instrument according to claim 17 wherein one of said locking parts has at least a portion that is deflectable to allow the handles to be placed in and released from the locking positions.

19. The surgical instrument according to claim 18 wherein the one locking part has a jaw that is pivotable between open and closed positions relative to the handle on which it is mounted and said jaw in its open position allows the handles to be placed in the one of their first and second relative positions whereupon the jaw can be moved to its closed position to place the handles in their locked position.

20. A surgical instrument comprising:
   an elongate body having a rear proximal end and a forward distal end;
   a grip assembly for holding and operating said surgical instrument,
   said grip assembly including a rear handle fixed to the body to define therewith a generally L shape,
   said rear handle being graspable by the hand of a user and having a back surface for reception in the palm of the hand of a user holding the surgical instrument,
   said grip assembly including a front handle that is pivotably connected to the rear handle for movement relative thereto between first and second relative positions;
   a working tip operating mechanism;
   a working tip mounted to at least one of said operating mechanism and body at a first location on said body for movement between first and second positions,
   said working tip comprising first and second jaws movable relative to each other between a first release position and a second gripping position,
   said jaws usable to grasp tissue with the jaws in their second gripping position; and
   means for connecting the front handle to the working tip operating mechanism for causing the working tip to move between its first and second positions as an incident of the handles moving between their first and second relative positions,
   the distal end of said elongate body being straight and projecting in a first line,
   said connecting means including means for allowing the working tip to be selectively rotated around the length of the first line to reposition the working tip relative to the body.

21. The surgical instrument according to claim 20 wherein the front handle has a loop to allow passage therethrough of a plurality of fingers of a user.

22. The surgical instrument according to claim 20 including means for releasably locking the handles in one of their first and second relative positions.

23. The surgical instrument according to claim 22 including a movable button and means mounting the button on one of the handles for movement to release the locking means.

24. The surgical instrument according to claim 22 including a button and means for mounting the button on the rear handle for movement between a normal position and a release position, said button being situated on the rear handle so as to be accessible by the finger on the hand of a user grasping the grip assembly.

25. The surgical instrument according to claim 20 wherein the working tip is pivotable about a second axis between its first and second positions and means are provided for permitting reorientation of the jaw axis relative to the body and rear handle.

26. A surgical instrument comprising:
   an elongate body having a rear proximal end and a forward distal end;
   a grip assembly for holding the surgical instrument;
   a working tip including first and second relatively movable jaws having cooperating gripping surfaces positionable selectively in a first release position and a second gripping position wherein tissue can be grasped between the jaws;
   a working top operating mechanism including an elongate operating rod;
   means for connecting the operating rod to at least one of the body and grip assembly for movement relative to the at least one of the body and grip assembly between first and second positions;
   cooperating means on the operating rod and working tip for positioning the working tip in its first position as an incident of the operating rod moving from one of its first and second positions into the other of its first and second positions, and for positioning the working tip in its second position as an incident of the operating rod moving from the other of its first and second positions into the one of its first and second positions; and
   means for allowing the operating rod to be rotated about its length to place the working tip selectively in a plurality of different positions relative to at least one of the body and grip assembly.

27. A surgical instrument comprising:
   an elongate body having a rear proximal end and a forward distal end;
   a grip assembly for holding the surgical instrument;
   a first working tip positionable selectively in first and second positions;
   a working tip operating mechanism including an elongate operating rod;
   means for connecting the operating rod to at least one of the body and grip assembly for movement relative to the at least one of the body and grip assembly between first and second positions;
   cooperating means on the operating rod and first working tip for positioning the first working tip in its first position as an incident of the operating rod moving from one of its first and second positions into the other of its first and second positions, and for positioning the first working tip in its second position as an incident of the operating rod moving from the other of its first and second positions into the one of its first and second positions; and
   means for releasably connecting the first working tip to the grip assembly to allow replacement of the first working tip.

28. The surgical instrument according to claim 27 in combination with a second working tip with means thereon for releasably connecting the second working tip to the grip assembly.

29. The surgical instrument according to claim 27 wherein said second working tip has a different configuration than said first working tip.

30. The surgical instrument according to claim 27 wherein said grip assembly includes a handle connected to the body so as to define a generally L-shape with said body.

* * * * *